United States Patent
Meskens et al.

(10) Patent No.: US 9,319,807 B2
(45) Date of Patent: Apr. 19, 2016

(54) DEVICE WITH COMBINED ANTENNA AND TRANSDUCER

(75) Inventors: Werner Meskens, Opwijk (BE); Jan Frieding, Leichhardt (AU); Ibrahim Bouchataoui, Mechelen (BE)

(73) Assignee: Cochlear Limited, Macquarie University (AU)

( * ) Notice: Subject to any disclaimer, the term of this patent is extended or adjusted under 35 U.S.C. 154(b) by 168 days.

(21) Appl. No.: 13/407,183

(22) Filed: Feb. 28, 2012

(65) Prior Publication Data
US 2013/0223664 A1 Aug. 29, 2013

(51) Int. Cl.
H04R 25/00 (2006.01)
A61N 1/372 (2006.01)
A61N 1/36 (2006.01)

(52) U.S. Cl.
CPC .......... H04R 25/554 (2013.01); A61N 1/37223 (2013.01); A61N 1/36032 (2013.01); H04R 25/606 (2013.01); H04R 2225/51 (2013.01); H04R 2225/63 (2013.01)

(58) Field of Classification Search
CPC .............................. H04R 25/554; H04R 25/00
USPC .............................. 381/312, 313, 315; 607/57
See application file for complete search history.

(56) References Cited

U.S. PATENT DOCUMENTS

| | | | |
|---|---|---|---|
| 6,115,636 A * | 9/2000 | Ryan | 607/60 |
| 6,437,750 B1 | 8/2002 | Grimes et al. | |
| 7,020,298 B1 | 3/2006 | Tziviskos et al. | |
| 7,142,926 B2 | 11/2006 | Crawford | |
| 7,515,881 B2 | 4/2009 | Essabar | |
| 2004/0073275 A1* | 4/2004 | Maltan et al. | 607/57 |
| 2004/0138723 A1* | 7/2004 | Malick et al. | 607/57 |
| 2005/0033383 A1* | 2/2005 | Ibrahim et al. | 607/57 |
| 2005/0251225 A1* | 11/2005 | Faltys et al. | 607/57 |
| 2007/0121979 A1* | 5/2007 | Zhu et al. | 381/315 |
| 2008/0253598 A1* | 10/2008 | Nielsen et al. | 381/330 |
| 2008/0304686 A1 | 12/2008 | Meskens et al. | |
| 2009/0110221 A1 | 4/2009 | Rithinger | |
| 2009/0169038 A1 | 7/2009 | Knudsen et al. | |
| 2010/0030012 A1 | 2/2010 | Meskens | |

FOREIGN PATENT DOCUMENTS

| | | |
|---|---|---|
| WO | 2005020549 A1 | 3/2005 |
| WO | 2007072381 A2 | 6/2007 |
| WO | 2009001234 A1 | 12/2008 |
| WO | 2009117778 A1 | 10/2009 |

* cited by examiner

*Primary Examiner* — Duc Nguyen
*Assistant Examiner* — Phan Le
(74) *Attorney, Agent, or Firm* — McDonnell Boehnen Hulbert & Berghoff LLP (57) ABSTRACT

A system includes an earhook having a connector for coupling to a behind-the-ear component of a hearing prosthesis. The earhook further includes a transducer and combined electromagnetic (EM) and magnetic induction (MI) antenna circuitry coupled to the transducer. The combined EM and MI antenna circuitry also includes an electrically conductive portion of the transducer and at least one inductor.

18 Claims, 5 Drawing Sheets

FIG. 5B

DEVICE WITH COMBINED ANTENNA AND TRANSDUCER

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound directly or indirectly to a person's bone or teeth, for example, thereby causing vibrations in the person's inner ear and bypassing the person's auditory canal and middle ear. Vibration-based hearing devices include, for example, bone anchored devices, direct acoustic cochlear stimulation devices, or other vibration-based devices. A bone-anchored device typically utilizes a surgically implanted mechanism or a passive connection through the skin or teeth to transmit vibrations corresponding to sound via the skull. A direct acoustic cochlear stimulation device also typically utilizes a surgically implanted mechanism to transmit vibrations corresponding to sound, but bypasses the skull and more directly stimulates the inner ear. Other non-surgical vibration-based hearing devices may use similar vibration mechanisms to transmit sound via direct or indirect vibration of teeth or other cranial or facial bones or structures.

Persons with certain forms of sensorineural hearing loss may benefit from hearing prostheses, such as cochlear implants and/or auditory brainstem implants. For example, cochlear implants can provide a person having sensorineural hearing loss with the ability to perceive sound by stimulating the person's auditory nerve via an array of electrodes implanted in the person's cochlea. A component of the cochlear implant detects sound waves, which are converted into a series of electrical stimulation signals that are delivered to the implant recipient's cochlea via the array of electrodes. Auditory brainstem implants can use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound.

Further, some persons may benefit from hearing prostheses that combine one or more characteristics of acoustic hearing aids, vibration-based hearing devices, cochlear implants, and auditory brainstem implants to enable the person to perceive sound. Such hearing prostheses can be referred to generally as hybrid hearing prostheses.

Various hearing prosthesis, such as those described generally above, are designed with separate units or components that are configured to communicate over a link with one other. The link between hearing prosthesis components can be a wired or wireless link that allows unidirectional or bidirectional communication and/or power transfer between components. In one example, a cochlear implant or a hybrid hearing prosthesis can include a first device that is generally disposed externally to the person and a second device that is at least partially implanted in the person. In the present example, the first device can be configured to detect sound, to encode the detected sound as acoustic signals, and to transmit the acoustic signals to the second device over a wireless link between the first and second devices. The second device is configured to receive the acoustic signals and to apply the acoustic signals as output signals to the person's hearing system. The output signals applied to the person's hearing system can include, for example, audible signals, vibrations, and electrical signals, as described generally above.

Generally, it is desirable to improve on the arrangements of the prior art or at least to provide one or more useful alternatives to facilitate communications between components of a medical or non-medical device and/or to facilitate communications between a medical or non-medical device and an external device.

SUMMARY

The present application is directed to providing wireless links for medical or non-medical devices. Generally, such wireless links may include an electromagnetic (EM) link and a magnetic induction (MI) link, which are implemented as part of a transducer system of a device. Further, in various non-limiting examples, the device can be a hearing prosthesis, such as a cochlear implant, a bone anchored device, a direct acoustic cochlear stimulation device, an auditory brain stem implant, an acoustic hearing aid, a hybrid hearing prosthesis, or any other type of hearing prosthesis configured to assist a recipient in perceiving sound.

Some embodiments of the present disclosure are directed to a system that includes an earhook having a connector for coupling to a behind-the-ear component of a hearing prosthesis. The earhook further includes a transducer and combined EM and MI antenna circuitry coupled to the transducer. The combined EM and MI antenna circuitry further includes an electrically conductive portion of the transducer and at least one inductor.

Yet other embodiments are directed to a system that includes a first hearing prosthesis device. The first hearing prosthesis device includes an interface for a second hearing prosthesis device that further includes a transducer system. The system also has a processor coupled to the first hearing prosthesis device and configured to generate control signals to control a plurality of functions that utilize the second hearing prosthesis device. The plurality of functions includes a first function of operating a transducer of the transducer system, a second function of operating an MI antenna of the transducer system, and a third function of operating an EM antenna of the transducer system.

Further embodiments are directed to a system that includes a first medical device that includes a processor and a first interface, and a second medical device that includes a transducer having a conductive body, a coil coupled to the transducer, and a second interface coupled to the coil. The first interface is removably coupled to the second interface. Further, the processor is configured to implement a first functionality of operating the transducer, a second functionality of operating a magnetic induction (MI) antenna, which includes, at least in part, the coil, and a third functionality of operating an electromagnetic (EM) antenna, which includes, at least in part, the conductive body.

DETAILED DESCRIPTION

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure.

Generally, the present disclosure is directed to combination transducer and antenna structures that facilitate wireless communications. For illustration purposes, some features and functions are described with respect to hearing prostheses. However, various features and functions disclosed herein may be applicable to other types of devices, including other types of medical and non-medical devices.

In one example, a hearing prosthesis includes a behind-the-ear (BTE) device that further includes a connector or interface for an auxiliary device, such as an earhook. In the present example, the earhook includes a transducer, which may include one or more of a speaker, microphone, light emitting element, telecoil, or other type of component that converts energy from one form to another. The connector for the auxiliary device has first and second contacts that correspond to contacts on a complementary connector of the auxiliary device. In the present example, the BTE device and the earhook include transducer and antenna circuitry that allows the BTE device to activate the transducer and to operate the transducer and antenna circuitry as an electromagnetic (EM) antenna and a magnetic induction (MI) antenna. The operation of the EM and MI antennas allows the BTE component and the earhook to communicate with external devices, such as another hearing prosthesis, an implant device, a remote computing device, etc.

Figure 1:
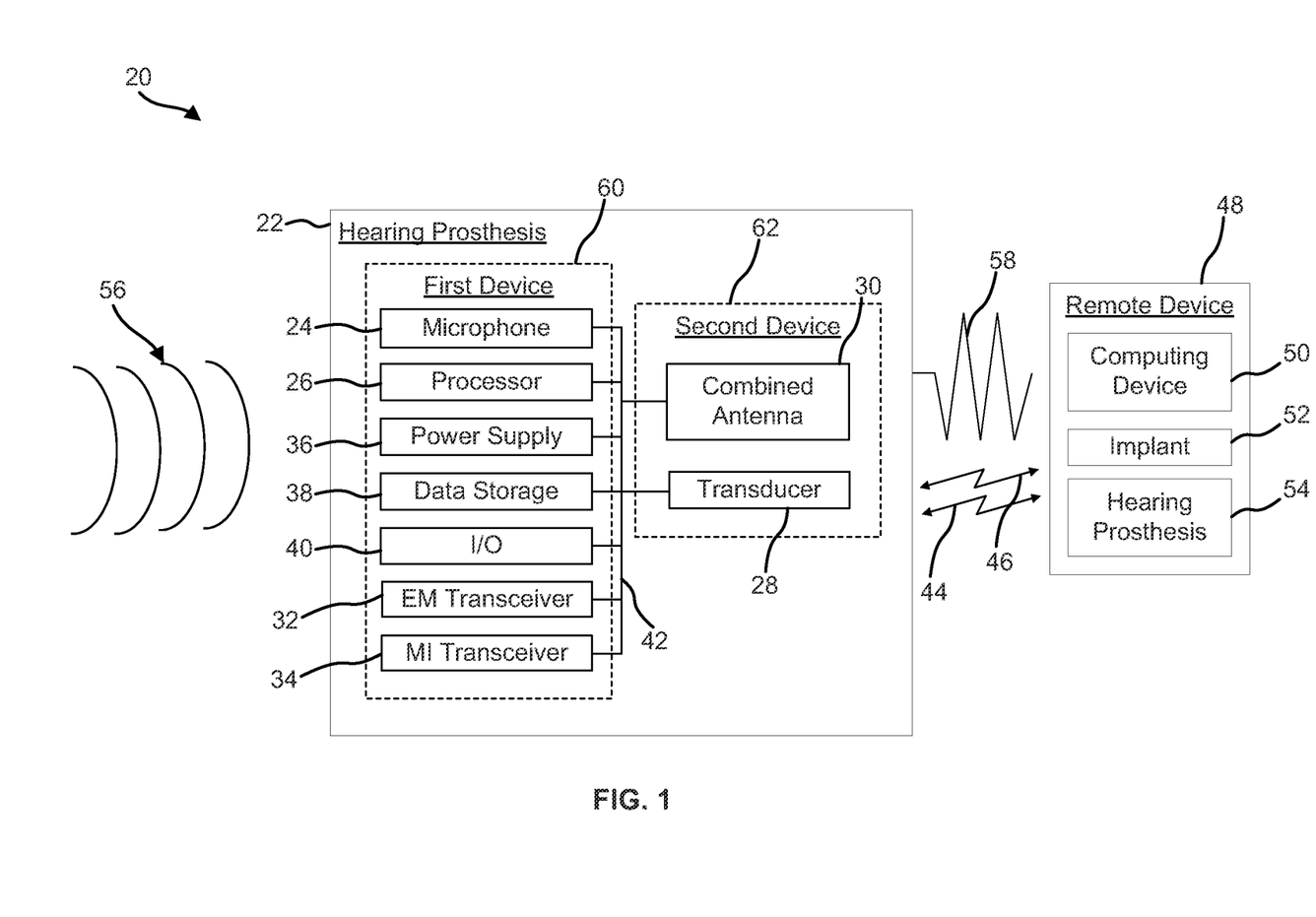
FIG. 1 illustrates a block diagram of a system including a combined antenna and a transducer according to an embodiment of the present disclosure.

Referring now to FIG. 1, an example system 20 includes a hearing prosthesis 22 configured according to some embodiments of the present disclosure. In various examples, the hearing prosthesis 22 can be a cochlear implant, an acoustic hearing aid, a bone-anchored device, a direct acoustic cochlear stimulation device, an auditory brainstem implant, a hybrid hearing prosthesis, or any other type of hearing prosthesis configured to assist a prosthesis recipient in perceiving sound.

The hearing prosthesis 22 illustrated in FIG. 1 includes a microphone 24, a processor 26, a transducer 28, combined antenna circuitry 30, an EM transceiver 32, an MI transceiver 34, a power supply 36, data storage 38, and one or more input/output (I/O) components or interfaces 40. The various components 24-40 can be directly or indirectly connected via a wired interface 42. In the present example, the EM transceiver 32 and the MI transceiver 34 are configured to enable an EM wireless radio frequency (RF) communication link 44 and an MI wireless RF communication link 46, respectively, to one or more remote devices 48. Various modifications can be made to the system 20 of FIG. 1, for example, the hearing prosthesis 22 may include one or more microphones 24, processors 26, transducers 28, power supplies 36, and/or data storage components 38.

The microphone 24 generally can include one or more omnidirectional and/or directional microphones so that the hearing prosthesis 22 can be configured to process background sounds and/or to focus on sounds from a specific direction, such as generally in front of the prosthesis recipient.

The processor 26 may include one or more general-purpose processors, such as microprocessors developed by Intel, ARM, Advanced Micro Devices, etc., and/or one or more special purpose processors, such as digital signal processors, application specific integrated circuits, etc. The processor 26 is configured to execute computer readable program instructions stored in the data storage 38 or otherwise accessible to the processor 26. Such instructions can be executed by the processor 26 to process audio signals, to control various components of the hearing prosthesis, and to communicate with remote devices, for example.

The data storage 38 includes computer readable storage media that can be read or accessed by the processor 26. The computer-readable storage media may include volatile and/or non-volatile storage components, such as optical, magnetic, organic, or other memory or disc storage, which can be integrated in whole or in part with the processor 26. Generally, the data storage 38 includes computer readable program instructions and perhaps additional data, such as user parameters for the hearing prosthesis 22.

The EM transceiver 32 and the MI transceiver 34 are configured to transmit and/or receive communications, signals, and other data over the EM link 44 and the MI link 46, respectively. In one example, the EM link 44 operates at frequencies above about 300 MHz and the MI link 46 operates at frequencies below about 30 MHz. As such, the transceivers 32, 34 can be used to facilitate communications between different devices and device components. Generally, the EM link 44 can be any suitable link, such as Bluetooth™, Bluetooth Low Energy™, Wi-Fi™, Zigbee™ operating in the 2.4 GHz industrial, scientific and medical (ISM) band, proprietary radio frequency links operating in the Medical Data Service (MEDS) and Medical Implant Communication Service (MICS) bands, and the like. Further, the MI link 46 is generally a radio frequency link that relates to a magnetic induction radio operating in the near field, as will be described in more detail hereinafter.

In the example of FIG. 1, the links 44, 46 can facilitate communications and other data transfer between the hearing prosthesis 22 and a remote device 48, which can include a computing device 50, an implant device 52 associated with the hearing prosthesis 22, and/or a second hearing prosthesis 54, for example. Generally, the computing device 50 can be utilized as a remote control for the hearing prosthesis 22 and to load data and instructions to the hearing prosthesis. As such, the computing device 50 may include suitable components, such as processors, I/O components, display devices, transceivers, data storage, power supply, etc.

Further, in one example, the hearing prosthesis 22 can communicate data with the implant device 52 over the links 44, 46. In the present example, the implant device 52 can utilize such communicated data to apply acoustic signals to an implant recipient's hearing system. In another example, the hearing prosthesis 22 can communicate with the second hearing prosthesis 54 to coordinate functions of each prosthesis and improve the ability of the recipient to perceive sound.

The I/O components 40 may include user interface controls, such as dials, switches, touchpads, and the like. Further, the I/O components 40 may include I/O interfaces for coupling to other devices or components, such as an earhook, headpiece coil, earphone, display devices, light emitting devices, and/or other devices now known or later developed.

The power supply 36 supplies power to various components of the hearing prosthesis 22 and can be any suitable power supply, such as a non-rechargeable or rechargeable battery. In one example, the power supply 36 is a battery that can be recharged wirelessly, such as through inductive charging. Such a wirelessly rechargeable battery would facilitate complete subcutaneous implantation of the hearing prosthesis 22 to provide a fully implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined, or otherwise, associated with use of the prosthesis.

Generally, in use, the microphone 24 is configured to receive acoustic signals 56 and the processor 26 is configured to process and convert such acoustic signals into output signals 58. In some examples, the processor 26 is configured to process and convert acoustic signals received from other sources, such as, a remote computing device or hearing prosthesis, into the output signals 58. The output signals 58 can then be applied to the implant recipient via the transducer 28, which can be, for example, a speaker or vibration mechanism. Alternatively or in conjunction, the output signals 58 can be communicated, such as over the links 44, 46, to the remote device 48, which can include the computing device 50, the implant device 52, and/or the second hearing prosthesis 54, for example. Illustratively, the output signals 58 are communicated over one or more of the links 44, 46 to the implant device 52, which applies the output signals to the implant recipient. Other examples are also possible and within the scope of the present disclosure.

The acoustic signals 56 are generally encoded into the output signals 58 in accordance with configuration settings or data developed for the prosthesis recipient. The configuration settings can be stored in the data storage 38. A recipient's configuration settings allow the hearing prosthesis 22 to be configured for or fitted to a recipient. Generally, the configuration settings include gain prescription rules and other configuration data that defines how the processor 26 of the prosthesis 22 converts the acoustic signals 56 received by the microphone 24 to output signals 58 that are applied, directly and/or indirectly, to the prosthesis recipient.

Various modifications can be made to the system 20 illustrated in FIG. 1. For example, the hearing prosthesis 22 may include additional or fewer components arranged in any suitable manner. In some examples, the hearing prosthesis 22 may include other components to process external audio signals, such as components that measure vibrations in the skull caused by audio signals and/or components that measure electrical outputs of portions of a person's hearing system in response to audio signals.

Further, depending on the type and design of the hearing prosthesis 22, the illustrated components may be enclosed within a single operational device or distributed across multiple operational devices, for example, two or more internal devices, two or more external devices, or combinations of one or more external devices and internal devices. Generally, an internal device can be hermetically sealed and adapted to be at least partially implanted in a person.

FIG. 1 further includes an example, illustrated in dashed lines, where the hearing prosthesis 22 can be divided into a first device 60 and a second device 62. In FIG. 1, the first device 60 includes the microphone 24, the processor 26, the EM transceiver 32, the MI transceiver 34, the power source 36, the data storage 38, and the I/O component 40. In the present example, the second device 62 includes the transducer 28 and the combined antenna circuitry 30. As will be described in more detail hereinafter, in some examples, the antenna circuitry 30 of the second device 62 can include at least a portion of the transducer 28. In other examples, the first and second devices 60, 62 can include additional or fewer components.

Figure 2:
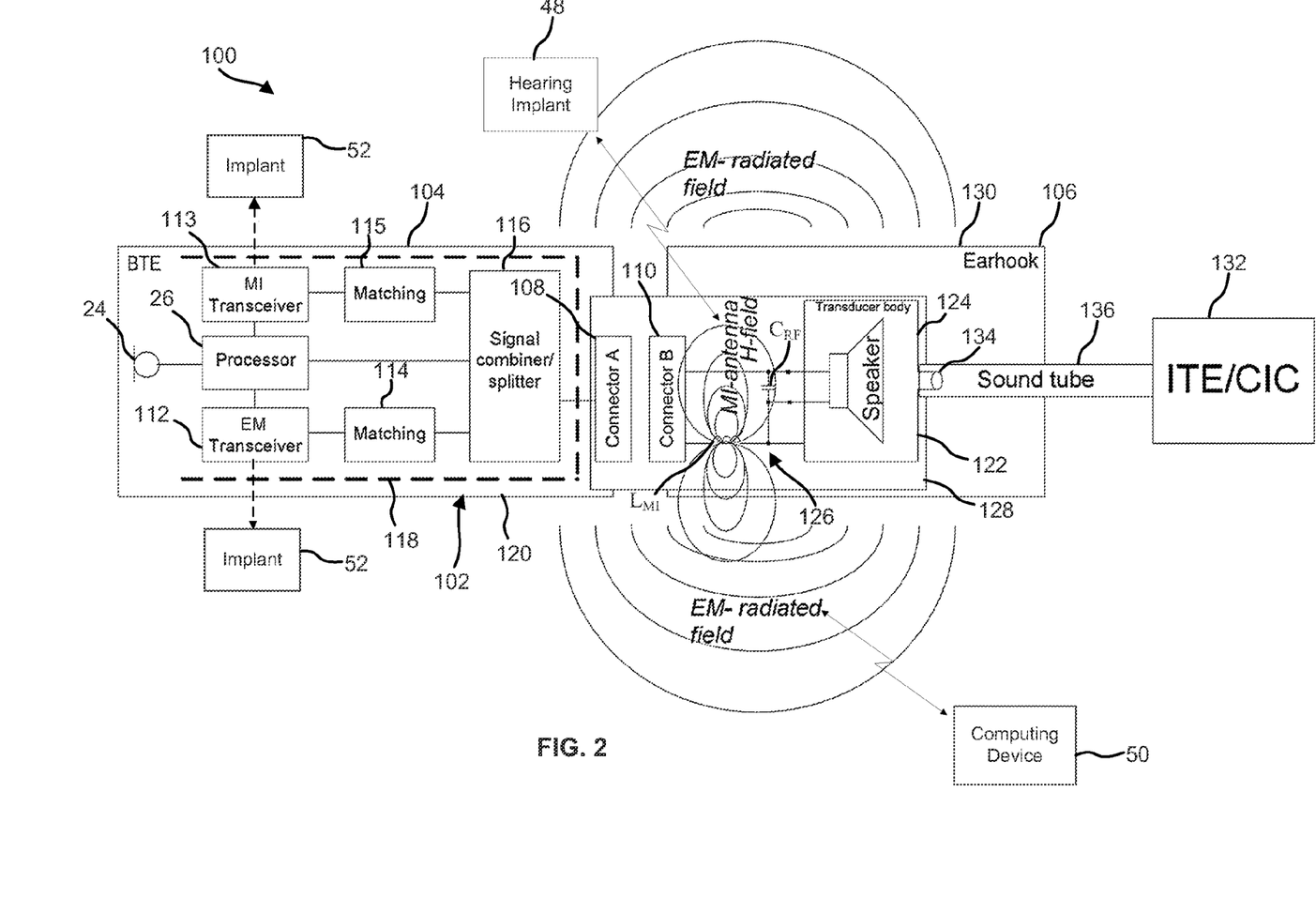
FIG. 2 illustrates another block diagram of a system including a combined antenna and a transducer according to an embodiment of the present disclosure.

Referring now to FIG. 2, a system 100 is illustrated that includes a hearing prosthesis 102, similar in structure and operation to the hearing prosthesis 22 of FIG. 1. The hearing prosthesis 102 of FIG. 2 includes a first device 104 that can be removably connected to a second device 106 utilizing a first connector or interface 108 coupled to the first device and a second connector or interface 110 coupled to the second device. Illustratively, the first device can be a BTE device and the second device can be an earhook that can be removably connected to the BTE device utilizing the connectors 108, 110, which provide a mechanical coupling and an electrical coupling between the devices.

Similarly to the first device 60 of FIG. 1, the first device 104 of FIG. 2 includes a microphone 24, a processor 26, an EM transceiver 112, and an MI transceiver 113. In FIG. 2, one or both of the transceivers 112, 113 can be configured to transmit acoustic output signals to an implant device 52. The first device 104 also includes first and second impedance matching circuits 114, 115, respectively, and a signal combiner/splitter 116, which will be described in more detail hereinafter. Generally, various components of the first device 104 can be disposed on a printed circuit board, which can further serve as a ground plane represented by the dashed line 118 and can be used as an RF ground plane by the EM transceiver 112, for example. In addition, various components of the first device 104 can be enclosed in a housing 120. FIG. 2 illustrates the microphone 24, the processor 26, the transceivers 112, 113, the impedance matching circuits 114, 115, the signal combiner/splitter 116, and the first connector 108 coupled together in one configuration, although, in other examples such configuration can be altered.

Similarly to the second device 62 of FIG. 1, the second device 106 of FIG. 2 includes a transducer 122, which further includes an electrically conductive body 124. The electrically conductive body 124 can totally or partially enclose the transducer 122, which in various non-limiting examples can include one or more of a speaker, a microphone, a telecoil, a light emitting element, etc. The second device 106 also includes transceiver or antenna circuitry 126. Portions of the transducer 122, the antenna circuitry 126, and the first and second connectors 108, 110 can be coupled together to form a combined antenna structure 128 that includes EM and MI antennas. As illustrated in FIG. 2, the antenna circuitry 126 can include a coil or inductor $L_{MI}$ and a capacitor $C_{RF}$. More particularly, in the example of FIG. 2, the inductor $L_{MI}$ can be coupled in series with the transducer 122 and the capacitor $C_{RF}$ can be coupled in parallel with the transducer. In addition, various components of the second device 106 can be enclosed in a housing 130.

FIG. 2 also illustrates an auxiliary device 132 that can be removably coupled to the second device 106 by a connector 134 to an air-interface 136 of the second device. Any suitable connector 134 can be utilized. In one example, the interface 136 is a sound tube and the auxiliary device 132 is a passive earphone, such as an in-the-ear or completely-in-the-canal earphone. Other examples are also possible and contemplated in the present disclosure.

Generally, in use, the hearing prosthesis 102 can be operated to perform a plurality of functions. A first function can include activating or operating the transducer 122, for example, operating a speaker to provide acoustic stimulation to a recipient's ear.

A second function can include operating the MI antenna of the combined antenna structure 128 to communicate with other devices. In the present example, the MI antenna of the combined antenna structure 128 includes the inductor $L_{MI}$. More particularly, the inductor $L_{MI}$ is configured to generate a magnetic field for communication with one or more remote devices, such as a second hearing implant 48.

A third function can include operating the EM antenna of the combined antenna structure 128 to communicate with other devices. More particularly, the EM antenna includes components within the first and second devices 104, 106, including one or more of the ground plane 118 and the conductive body 124 of the transducer 122. Illustratively, the EM antenna radiates an EM field for communication with one or more remote devices, such as the computing device 50.

Additional functions are also contemplated, such as operating the transceivers 112, 113 to communicate with the implant 52.

Referring to the first, second, and third functions described above, generally, the processor 26 of the first device generates control signals for execution of each function. The processor 26 can generate different control signals for each function and such control signals can be transmitted or sent substantially simultaneously or intermittently through the connectors 108, 110 to the second device 106. Consequently, the different functions can be executed substantially simultaneously or intermittently, as needed or desired. In one example, the signal combiner/splitter 116 facilitates substantially simultaneous transmission of multiple control signals by combining different control signals for each function into a single control signal that can be applied to the second device 106 through the connectors 108, 110. Illustratively, the signal combiner/splitter 116 can be any suitable diplexer, triplexer, multiplexer, and the like for unidirectional or bidirectional data transfer.

In another example, the signal combiner/splitter 116 receives a signal from the second device 106. In the present example, the received signal may include multiple components associated with different functions and the signal combiner/splitter 116 can split the signal into the respective components for processing in accordance with different functions.

In addition, the impedance matching circuits 114,115 can be provided and configured to improve the antenna efficiency of the combined antenna structure 128.

Further, signals for the first, second, and third functions can be separated into different frequency bands or ranges to help avoid interference between the signals. In one example, the operating frequency $F_1$ for the first function is less than the operating frequency $F_2$ for the second function, which is less than the operating frequency $F_3$ for the third function. In another example, $F_2$ is greater than about $100F_1$ and $F_3$ is greater than about $10F_2$. In other examples, $F_1$ can be between about DC (0 Hz) and 9 KHz, $F_2$ can be between about 9 KHz and 30 MHz, and $F_3$ can be greater than about 300 MHz.

In yet other examples, control signals for the first function at the operating frequency $F_1$ may include bidirectional audio signals (such as PWM and S/D signals for driving a speaker), light control signals, telecoil signals, and the like. Further, control signals for the second function at the operating frequency $F_2$ may include bidirectional or unidirectional MI radio signals and control signals for the third function at the operating frequency $F_3$ may include bidirectional or unidirectional EM radio signals.

Figure 3A:
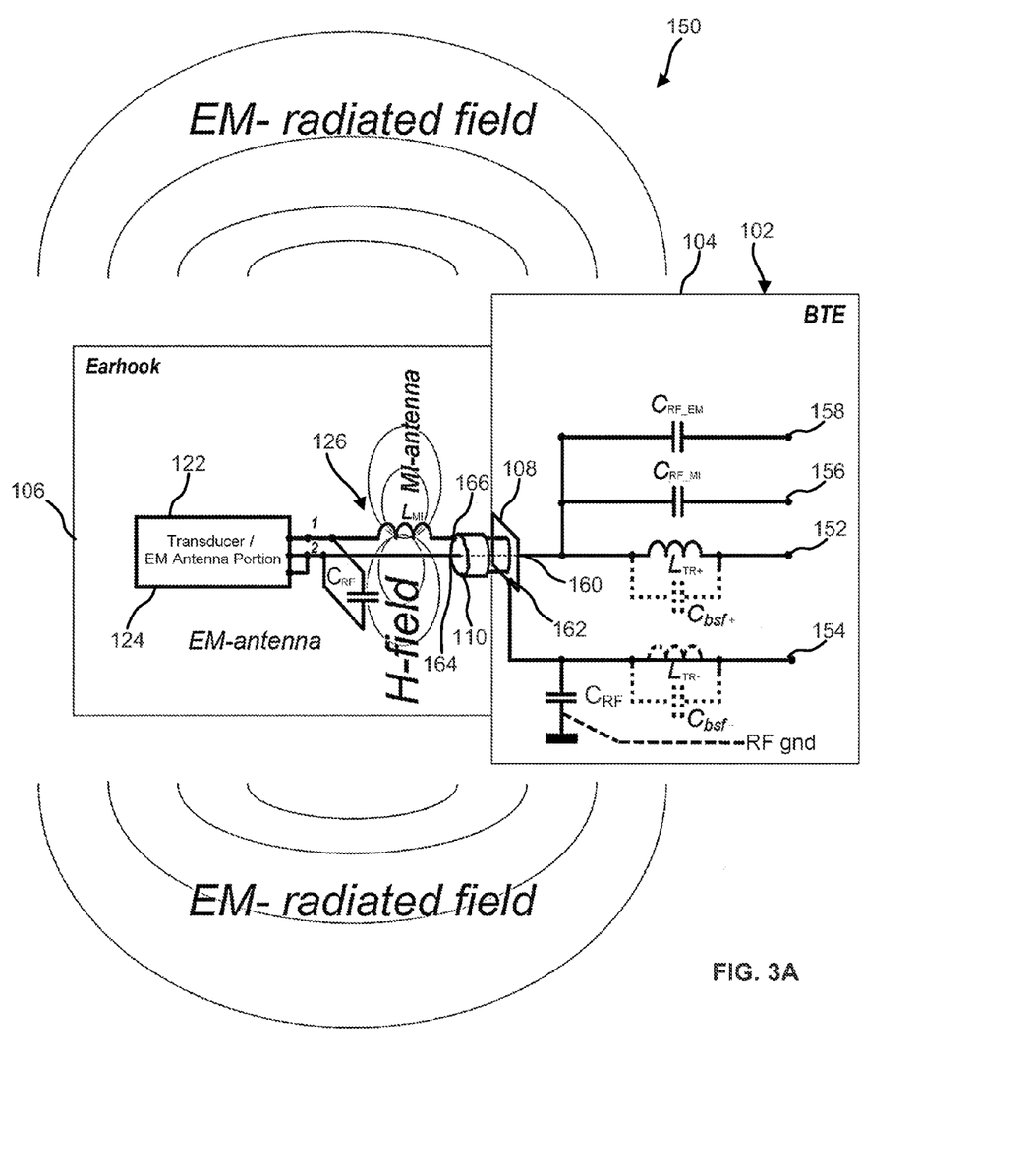
FIG. 3A illustrates a partial electrical schematic, partial block diagram of a system including a combined antenna, a transducer, and a coaxial connection according to an embodiment of the present disclosure.

FIG. 3A illustrates another system 150 similar to the system 100 of FIG. 2 with additional circuitry details that can be utilized to facilitate execution of the first, second, and third functions discussed herein. More particularly, the first function can generally be executed utilizing first and second conductive paths or wires 152, 154, respectively. In one example, controls signals or acoustic output signals can be applied to the first conductive path 152 to operate the transducer 122. In the present example, the first conductive path 152 is coupled to the transducer 122 through an inductor $L_{TR+}$ that is configured to block or isolate MI and/or EM RF control signals for the second and third functions, respectively. A band stop filter, including a capacitor $C_{bsf+}$, can also be coupled in parallel with the inductor $L_{TR+}$ to increase the isolation from EM and/or MI control signals. Such isolation between the control signals for the first function at the operating frequency $F_1$ and the MI and EM control signals for the second and third functions at the operating frequencies $F_2$, $F_3$, respectively, facilitate proper operating and efficient transfer of signals to and/or from the combined antenna structure 128 and the transducer 122.

Control signals or acoustic output signals can also be applied to the second conductive path 154 for differential operation of the first function. Further, as illustrated in the system 150 of FIG. 3A, the second conductive path 154 may also include an inductor $L_{TR-}$ and a band stop filter including a capacitor $C_{bsf-}$, both illustrated in dashed lines. The system 150 also includes a capacitor $C_{RF}$ that provides a connection to ground, which can be used for MI and EM control signals of the second and third functions.

The second function can be generally executed utilizing a third conductive path 156. More particularly, controls signals can be applied to the third conductive path 156 to operate the MI antenna. In the present example, the third conductive path 156 can be coupled to the antenna circuitry 126 through a capacitor $C_{RF\_MI}$. More particularly, the control signal applied to the third conductive path 156 can be an electrically modulated alternating current signal applied to the inductor $L_{MI}$. Such alternating current signal applied to the third conductive path 156 causes the inductor $L_{MI}$ to generate an H-field that allows near-field communication often referred to as MI-radio communication when the MI field is modulated in amplitude, frequency, phase, or any combination thereof. The inductor $L_{MI}$ is also referred to as an MI loop antenna or an MI coil antenna. Signals can be received through the MI antenna by decoding voltage signals induced in the inductor $L_{MI}$ by an external H-field. To facilitate the reception of signals through the MI antenna, a parallel resonant tank including a capacitor connected in parallel (not shown) can be coupled to the third conductive path 156 and RF ground. Alternating between transmitting and receiving with the MI antenna can be implemented through suitable switching components (not shown) to change between series and parallel capacitor circuitry and capacitor values, as needed.

Generally, the inductor $L_{MI}$ functions as a high impedance electrical circuit for EM control signals of the third function at the frequency $F_3$. Further, the capacitor $C_{RF}$ can be included to act as a low impedance component or electrical short circuit for RF control signals of the second and third functions at the frequencies $F_2$ and $F_3$.

The third function can be generally executed utilizing a fourth conductive path 158. More particularly, control signals can be applied to the fourth conductive path 158 to operate the EM antenna. In the present example, the fourth conductive path 158 can be coupled to the antenna circuitry 126 through a capacitor $C_{RF\_EM}$. Generally, the EM field can be radiated by any suitable EM antenna, for example, an open (Hertzian) monopole, dipole, a resonant Lambda/4 groundplane antenna, and the like. In one example, for a resonant groundplane antenna, the second conductive path 154 can serve as the ground connection. In another example, for an open monopole or dipole antenna, the conductive body 124 of the transducer 122 serves as the radiating part of the antenna structure.

FIG. 3A also illustrates additional details of the connectors 108, 110. More particularly, the first connector 108 includes first and second contacts 160, 162, respectively, and the second connector 110 includes complimentary first and second contacts 164, 166, respectively. The first and second connectors 108, 110 and the first and second contacts 160-166 can be used to implement at least the first, second, and third functionalities described herein. However, in other examples, additional connectors and/or contacts can be used to implement the functions disclosed herein and other functions not disclosed herein.

Figure 3B:
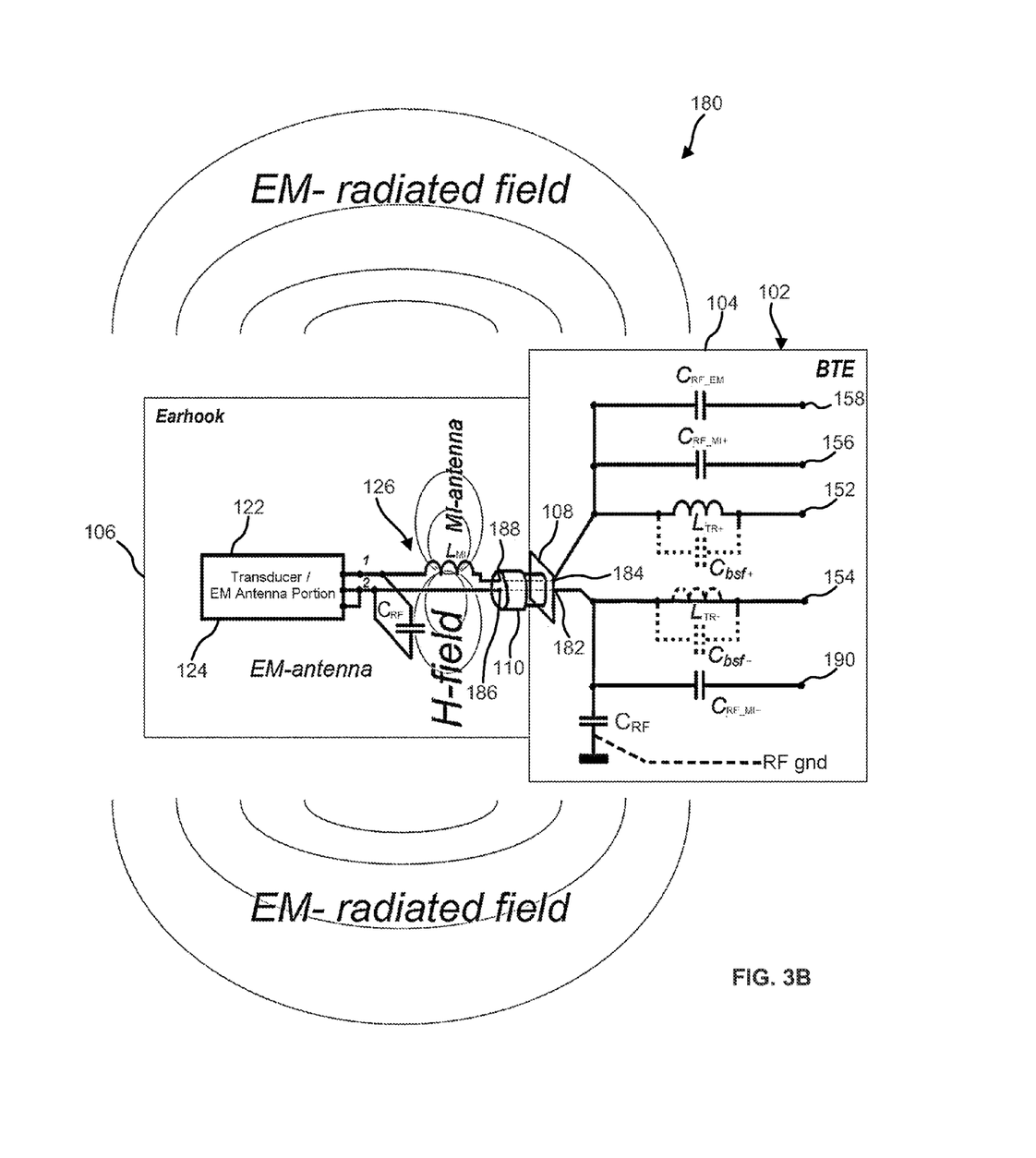
FIG. 3B illustrates a partial electrical schematic, partial block diagram of a system including a combined antenna, a transducer, and a twin-axial connection according to an embodiment of the present disclosure.

FIG. 3B illustrates another system 180, which is similar to the system 150 of FIG. 3A, but which includes a twin-axial connection and a differential/symmetrical MI control signal in and/or output constructions. More particular, the twin-axial connection includes connector 108, which has first and second contacts 182, 184, respectively, and the second connector 100, which has complimentary first and second contacts 186, 188, respectively. In the present example, the first, third, and fourth conductive paths 152, 156, and 158 are coupled to the second contact 184, as shown in FIG. 3B and the second conductive path 154 and the ground plane are coupled to the first contact 182. Other connections are possible in other examples.

The differential/symmetrical MI control signal in the system 180 can be applied a fifth conductive path 190. In the present example, the fifth conductive path 190 can be coupled to the antenna circuitry 126 through a capacitor $C_{RF\_MI-}$ and the third conductive path 156 can be coupled to the antenna circuitry 125 through a capacitor $C_{RF\_MI+}$. Further, in the present example, the fifth conductive path 190 is coupled to the second contact 184.

Figure 4:
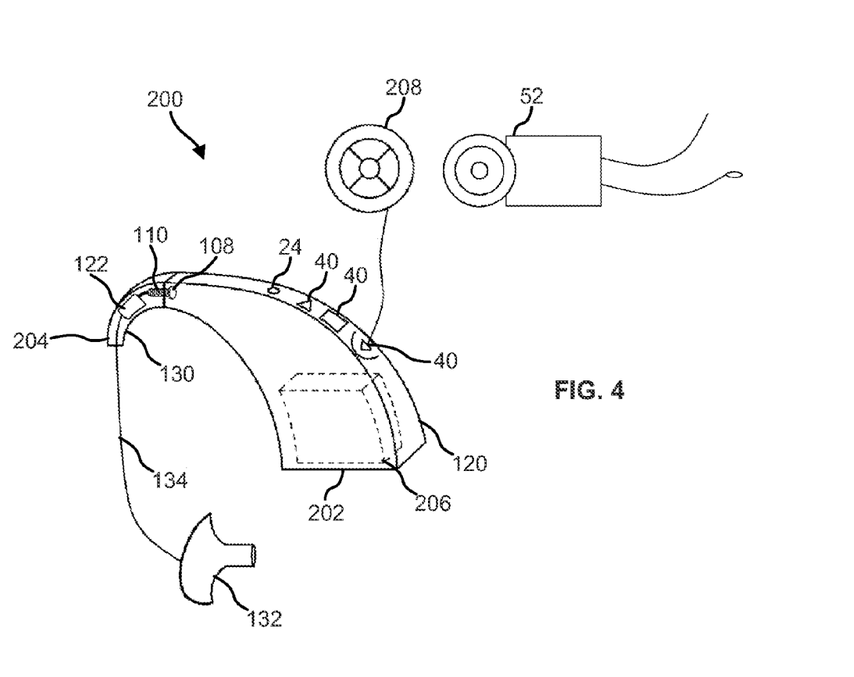
FIG. 4 shows a hearing prosthesis with a behind-the-ear device, an earhook, and various other devices in accordance with an embodiment of the present disclosure.
Figure 5A:
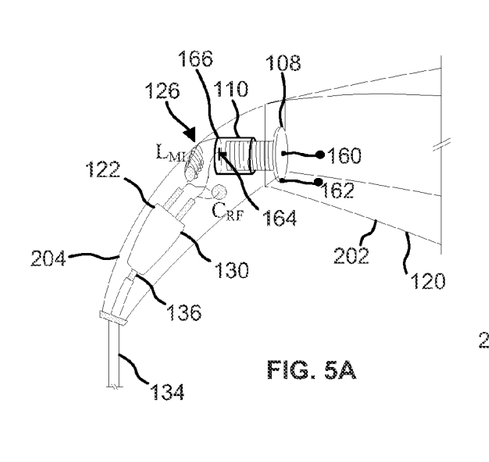
FIG. 5A illustrates an enlarged view of a connection between the behind-the-ear device and the earhook of FIG. 4.
Figure 5B:
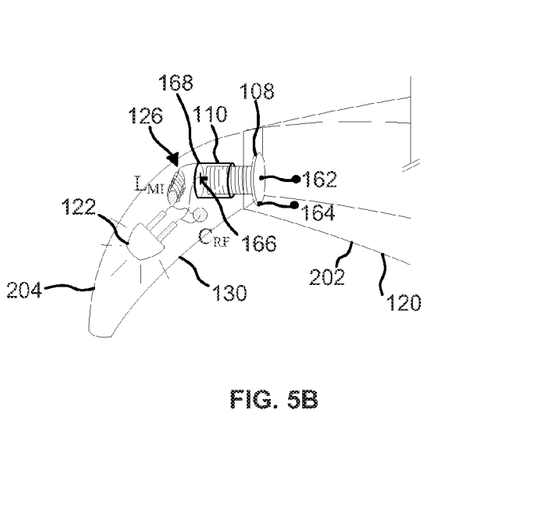
FIG. 5B illustrates another enlarged view of a connection between a behind-the-ear device and an earhook, which includes a light emitting transducer.

Referring now to FIGS. 4, 5A, and 5B, an example hearing prosthesis system 200 is illustrated. In FIG. 4, the hearing prosthesis system 200 includes a BTE device 202 and an earhook 204. The BTE device 202 includes various components, such as microphone 24, I/O components or interfaces 40, a first connector 108, and various internal components 206, which may include, for example, a processor, a transceiver, a power supply, and data storage, as described above. Referring more particularly to FIGS. 4, 5A, and 5B, the earhook 204 includes various components, such as a second connector 110, a transducer 122, antenna circuitry 126, which includes an inductor $L_{MI}$ and a capacitor $C_{RF}$, and an interface 136 for an auxiliary device 132 (shown in FIG. 5A).

FIG. 4 further illustrates the auxiliary device 132 coupled to the earhook 204 by a connection 134. In addition, a headpiece coil 208 is connected to the BTE device 202 by a connector 210. Generally, in use, the headpiece coil 208 can be utilized to communicate wirelessly with the implant 52 to apply electric signals to a recipient's hearing system.

FIG. 5A further illustrates a magnified view of the first and second connectors 108, 110, and the first and second contacts 160-166. Generally, the first and second contacts can be configured as a co-axial or twin-axial plug or socket that mechanically and electrically couples the BTE device 202 and the earhook 204.

FIG. 5B further illustrates an example of the earhook 204, which includes a combined antenna structure having an LED as the transducer 122.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system comprising:
   an earhook having a connector for coupling to a behind-the-ear component of a hearing prosthesis, wherein the earhook further includes:
   a transducer including an electrically conductive body, and
   combined electromagnetic (EM) and magnetic induction (MI) antenna circuitry, wherein the combined EM and MI antenna circuitry includes the electrically conductive body of the transducer and at least one inductor, wherein the electrically conductive body of the transducer is an EM field radiating part of the combined EM and MI antenna circuitry, wherein the at least one inductor of the combined EM and MI antenna circuitry is configured as an MI antenna when control signals are applied to the combined EM and MI antenna circuitry in a first radio frequency (RF) band and the at least one inductor is configured as an electrical open circuit when control signals are applied to the combined EM and MI antenna circuitry in a second RF band, wherein the first RF band is lower than the second RF band.

2. The system of claim 1, wherein the transducer includes one or more of a speaker, a microphone, a light emitting element, or a telecoil.

3. The system of claim 1, wherein the first RF frequency band is less than about 30 MHz and the second RF frequency band is greater than about 300 MHz.

4. The system of claim 1, wherein the connector includes first and second contacts configured to implement a plurality of functions utilizing the transducer and the combined EM and MI antenna circuitry.

5. The system of claim 4, wherein the plurality of functions includes operating the transducer, operating the combined EM and MI antenna circuitry as an EM antenna, and operating the combined EM and MI antenna circuitry as an MI antenna.

6. A system comprising:
a first hearing prosthesis device, wherein the first hearing prosthesis device includes an interface for a second hearing prosthesis device, wherein the second hearing prosthesis device includes a transducer system, wherein the interface includes first and second contacts configured to engage with complimentary contacts of the second hearing prosthesis device, and wherein the first contact is further configured to be coupled to first, second and third conductive paths of the second hearing prosthesis device;
a processor coupled to the first hearing prosthesis device and configured to generate different control signals that are applied to the first and second contacts to control a plurality of different functions that utilize the second hearing prosthesis device, wherein the control signals include first, second, and third control signals for application to the first, second, and third conductive paths, respectively, to implement first, second, and third functions, respectively, wherein the plurality of functions includes the first function of operating a transducer of the transducer system, the second function of operating a magnetic induction (MI) antenna of the transducer system, and the third function of operating an electromagnetic (EM) antenna of the transducer system;
means for combining the different control signals into a single control signal for application to the first contact; and
means for splitting different data signals received at the first contact from the second hearing prosthesis device, wherein the different data signals are associated with different functions, and wherein the processor is configured to process the different data signals in accordance with the different functions.

7. The system of claim 6, wherein the second and third functions include transmitting and receiving communications utilizing the EM antenna and the MI antenna.

8. The system of claim 6, further comprising an inductor coupled between the first conductive path and the first contact.

9. The system of claim 8, further comprising a band stop filter coupled between the first conductive path and the first contact.

10. The system of claim 6, further comprising a ground plane coupled to the second contact.

11. A system comprising:
a first medical device that includes a processor and a first interface, wherein the first interface includes first and second contacts; and
a second medical device that includes a transducer, a coil coupled to the transducer, and a second interface coupled to the coil, wherein the second interface includes third and fourth contacts, wherein the first contact is configured to be removably coupled to the third contact and the second contact is configured to be removably coupled to the fourth contact, and wherein first, second, and third conductive paths are coupled to the third contact,
wherein the processor is configured to:
generate a first control signal for application to the first conductive path to implement a first functionality of operating the transducer,
generate a second control signal for application to the second conductive path to implement a second functionality of operating a magnetic induction (MI) antenna, wherein the MI antenna includes, at least in part, the coil, and
generate a third control signal for application to the third conductive path to implement a third functionality of operating an electromagnetic (EM) antenna, wherein operating the EM antenna includes, at least in part, using a conductive body of the transducer as an EM field radiating component.

12. The system of claim 11, wherein the transducer includes one or more of a speaker, a microphone, a light emitting element, or a telecoil.

13. The system of claim 11, wherein the second and third functionalities include transmitting and receiving communications utilizing the EM antenna and the MI antenna.

14. The system of claim 11, wherein the first, second, and third control signals are encoded in different first, second, and third frequency bands, respectively.

15. The system of claim 14, wherein the first frequency band is between about 1 Hz and 50 KHz, the second frequency band is between about 200 KHz and 30 MHz, and the third frequency band is greater than about 300 MHz.

16. The system of claim 11, wherein the processor is configured to generate different electrical signals for different functionalities, and wherein the system further includes a signal combiner for combining the different electrical signals into single electrical signal for application to the first contact.

17. The system of claim 16, wherein the first contact is configured to receive different electrical signals associated with different functionalities, and wherein the system further includes a signal splitter for splitting the different electrical signals for processing by the processor in accordance with each different functionality.

18. The system of claim 6, wherein the first hearing prosthesis device is a behind-the-ear component, and the second hearing prosthesis device is an earhook.

* * * * *